United States Patent
Dong et al.

(10) Patent No.: US 9,008,771 B2
(45) Date of Patent: *Apr. 14, 2015

(54) NON-CAPTURED INTRINSIC DISCRIMINATION IN CARDIAC PACING RESPONSE CLASSIFICATION

(75) Inventors: Yanting Dong, Shoreview, MN (US);
Scott A. Meyer, Rochester, MN (US);
Kevin John Stalsberg, White Bear Lake, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 272 days.

This patent is subject to a terminal disclaimer.

(21) Appl. No.: 13/411,852

(22) Filed: Mar. 5, 2012

(65) Prior Publication Data

US 2012/0165895 A1 Jun. 28, 2012

Related U.S. Application Data

(63) Continuation of application No. 12/217,652, filed on Jul. 7, 2008, now Pat. No. 8,145,310, which is a continuation of application No. 11/116,558, filed on Apr. 28, 2005, now abandoned, and a (Continued)

(51) Int. Cl.
*A61N 1/37* (2006.01)
*A61B 5/0452* (2006.01)

(52) U.S. Cl.
CPC ............. *A61N 1/371* (2013.01); *A61B 5/04525* (2013.01)

(58) Field of Classification Search
CPC ... A61N 1/371; A61N 1/3712; A61N 1/3627; A61N 1/365; A61N 1/3702; A61N 1/3704; A61N 1/37; A61B 5/04525; A61B 5/7264; A61B 5/0452; A61B 5/04012; A61B 5/7246

USPC .................. 607/27–28, 4–5, 9; 600/509–510
See application file for complete search history.

(56) References Cited

U.S. PATENT DOCUMENTS

| 3,920,005 A | 11/1975 | Gombrich et al. |
| 4,023,564 A | 5/1977 | Valiquette et al. |

(Continued)

FOREIGN PATENT DOCUMENTS

| EP | 0468720 | 1/1992 |
| EP | 0560569 | 9/1993 |

(Continued)

OTHER PUBLICATIONS

Acar et al., "SVD-based on-line exercise ECG signal orthogonalization," *IEEE Transactions on Biomedical Engineering*, vol. 46, No. 3, Mar. 1999. Abstract only.

(Continued)

*Primary Examiner* — Carl H Layno
*Assistant Examiner* — Jennifer Ghand
(74) *Attorney, Agent, or Firm* — Seager, Tufte & Wickhem, LLC

(57) ABSTRACT

Cardiac devices and methods discriminate non-captured intrinsic beats during evoked response detection and classification by comparing the features of a post-pace cardiac signal with expected features associated with a non-captured response with intrinsic activation. Detection of a non-captured response with intrinsic activation may be based on the peak amplitude and timing of the cardiac signal. The methods may be used to discriminate between a fusion or capture beat and a non-captured intrinsic beat. Discriminating between possible cardiac responses to the pacing pulse may be useful, for example, during automatic capture verification and/or a capture threshold test.

20 Claims, 7 Drawing Sheets

Related U.S. Application Data continuation-in-part of application No. 12/008,876, filed on Jan. 15, 2008, now Pat. No. 8,831,726, which is a continuation of application No. 10/733,869, filed on Dec. 11, 2003, now Pat. No. 7,319,900.

(56) References Cited

U.S. PATENT DOCUMENTS

| | | |
|---|---|---|
| 4,340,063 A | 7/1982 | Maurer |
| 4,364,396 A | 12/1982 | Barthel |
| 4,365,636 A | 12/1982 | Barker |
| 4,458,692 A | 7/1984 | Simson |
| 4,476,869 A | 10/1984 | Bihn |
| 4,550,221 A | 10/1985 | Mabusth |
| 4,552,154 A | 11/1985 | Hartlaub |
| 4,562,841 A | 1/1986 | Brockway et al. |
| 4,573,481 A | 3/1986 | Bullara |
| 4,648,407 A | 3/1987 | Sackner |
| 4,680,708 A | 7/1987 | Ambos et al. |
| 4,686,332 A | 8/1987 | Greanias et al. |
| 4,827,935 A | 5/1989 | Geddes et al. |
| 4,860,766 A | 8/1989 | Sackner |
| 4,878,497 A | 11/1989 | Callaghan et al. |
| 4,928,688 A | 5/1990 | Mower |
| 4,953,551 A | 9/1990 | Mehra et al. |
| 4,979,507 A | 12/1990 | Heinz |
| 5,000,189 A | 3/1991 | Throne et al. |
| 5,033,467 A | 7/1991 | Bocchi et al. |
| 5,036,849 A | 8/1991 | Hauck et al. |
| 5,101,831 A | 4/1992 | Koyama et al. |
| 5,105,354 A | 4/1992 | Nishimura |
| 5,133,353 A | 7/1992 | Hauser |
| 5,146,918 A | 9/1992 | Kallok et al. |
| 5,170,784 A | 12/1992 | Ramon et al. |
| 5,178,156 A | 1/1993 | Takishima et al. |
| 5,179,945 A | 1/1993 | Van Hofwegen et al. |
| 5,184,615 A | 2/1993 | Nappholz et al. |
| 5,187,657 A | 2/1993 | Forbes |
| 5,203,348 A | 4/1993 | Dahl et al. |
| 5,209,229 A | 5/1993 | Gilli |
| 5,217,021 A | 6/1993 | Steinhaus et al. |
| 5,222,493 A | 6/1993 | Sholder |
| 5,230,337 A | 7/1993 | Dahl et al. |
| 5,233,983 A | 8/1993 | Markowitz |
| 5,261,400 A | 11/1993 | Bardy |
| 5,271,411 A | 12/1993 | Ripley et al. |
| 5,273,035 A | 12/1993 | Markowitz et al. |
| 5,284,136 A | 2/1994 | Hauck et al. |
| 5,292,338 A | 3/1994 | Bardy |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,324,310 A | 6/1994 | Greeninger et al. |
| 5,331,966 A | 7/1994 | Bennett et al. |
| 5,331,996 A | 7/1994 | Ziehm |
| 5,333,095 A | 7/1994 | Stevenson et al. |
| 5,334,222 A | 8/1994 | Salo et al. |
| 5,335,657 A | 8/1994 | Terry, Jr. et al. |
| 5,350,410 A | 9/1994 | Kleks et al. |
| 5,353,788 A | 10/1994 | Miles |
| 5,360,442 A | 11/1994 | Dahl et al. |
| 5,366,496 A | 11/1994 | Dahl et al. |
| 5,372,606 A | 12/1994 | Lang et al. |
| 5,374,280 A | 12/1994 | den Dulk |
| 5,376,106 A | 12/1994 | Stahmann et al. |
| 5,376,476 A | 12/1994 | Eylon |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,529 A | 5/1995 | Hudrlik |
| 5,411,533 A | 5/1995 | Dubreuil |
| 5,411,539 A | 5/1995 | Neisz |
| 5,431,693 A | 7/1995 | Schroeppel |
| 5,439,482 A | 8/1995 | Adams et al. |
| 5,441,518 A | 8/1995 | Adams et al. |
| 5,443,485 A | 8/1995 | Housworth et al. |
| 5,447,519 A | 9/1995 | Peterson |
| 5,468,254 A | 11/1995 | Hahn et al. |
| 5,485,851 A | 1/1996 | Erickson |
| 5,517,983 A | 5/1996 | Deighan et al. |
| 5,520,191 A | 5/1996 | Karlsson et al. |
| 5,522,860 A | 6/1996 | Molin et al. |
| 5,531,779 A | 7/1996 | Dahl et al. |
| 5,534,017 A | 7/1996 | van Krieken et al. |
| 5,540,727 A | 7/1996 | Tockman et al. |
| 5,540,732 A | 7/1996 | Testerman |
| 5,545,186 A | 8/1996 | Olson et al. |
| 5,545,202 A | 8/1996 | Dahl et al. |
| 5,549,655 A | 8/1996 | Erickson |
| 5,591,216 A | 1/1997 | Testerman et al. |
| 5,603,732 A | 2/1997 | Dahl et al. |
| 5,620,466 A | 4/1997 | Haefner et al. |
| 5,626,620 A | 5/1997 | Kieval et al. |
| 5,634,938 A | 6/1997 | Swanson et al. |
| 5,641,326 A | 6/1997 | Adams |
| 5,650,759 A | 7/1997 | Hittman et al. |
| 5,658,318 A | 8/1997 | Stroetmann et al. |
| 5,662,688 A | 9/1997 | Haefner et al. |
| 5,662,696 A | 9/1997 | Kroll et al. |
| 5,674,254 A | 10/1997 | van Krieken |
| 5,683,431 A | 11/1997 | Wang |
| 5,683,434 A | 11/1997 | Archer |
| 5,697,953 A | 12/1997 | Kroll et al. |
| 5,697,956 A | 12/1997 | Bornzin |
| 5,704,365 A | 1/1998 | Albrecht et al. |
| 5,713,933 A | 2/1998 | Condie et al. |
| 5,715,812 A | 2/1998 | Deighan et al. |
| 5,718,720 A | 2/1998 | Prutchi et al. |
| 5,724,984 A | 3/1998 | Arnold et al. |
| 5,735,883 A | 4/1998 | Paul et al. |
| 5,738,102 A | 4/1998 | Lemelson |
| 5,779,645 A | 7/1998 | Olson et al. |
| 5,814,087 A | 9/1998 | Renirie |
| 5,817,027 A | 10/1998 | Arand et al. |
| 5,827,326 A | 10/1998 | Kroll et al. |
| 5,836,987 A | 11/1998 | Baumann et al. |
| 5,844,506 A | 12/1998 | Binstead |
| 5,855,593 A | 1/1999 | Olson et al. |
| 5,857,977 A | 1/1999 | Caswell et al. |
| 5,860,918 A | 1/1999 | Schradi et al. |
| 5,861,011 A | 1/1999 | Stoop |
| 5,861,013 A | 1/1999 | Peck et al. |
| 5,871,512 A | 2/1999 | Hemming et al. |
| 5,873,898 A | 2/1999 | Hemming et al. |
| 5,876,353 A | 3/1999 | Riff |
| 5,895,414 A | 4/1999 | Sanchez-Zambrano |
| 5,916,243 A | 6/1999 | KenKnight et al. |
| 5,944,680 A | 8/1999 | Christopherson et al. |
| 5,957,956 A | 9/1999 | Kroll et al. |
| 5,964,778 A | 10/1999 | Fugoso et al. |
| 5,974,340 A | 10/1999 | Kadhiresan |
| 5,987,352 A | 11/1999 | Klein et al. |
| 6,026,320 A | 2/2000 | Carlson et al. |
| 6,038,474 A | 3/2000 | Zhu et al. |
| 6,044,298 A | 3/2000 | Salo et al. |
| 6,045,513 A | 4/2000 | Stone et al. |
| 6,049,730 A | 4/2000 | Kristbjarmarson |
| 6,052,620 A | 4/2000 | Gillberg et al. |
| 6,055,454 A | 4/2000 | Heemels |
| 6,064,910 A | 5/2000 | Andersson et al. |
| 6,076,014 A | 6/2000 | Alt |
| 6,076,015 A | 6/2000 | Hartley et al. |
| 6,084,253 A | 7/2000 | Turner, Jr. |
| 6,091,973 A | 7/2000 | Colla et al. |
| 6,101,416 A | 8/2000 | Sloman |
| 6,115,628 A | 9/2000 | Stadler et al. |
| 6,120,441 A | 9/2000 | Griebel |
| 6,126,611 A | 10/2000 | Bourgeois et al. |
| 6,128,534 A | 10/2000 | Park et al. |

(56) References Cited

U.S. PATENT DOCUMENTS

| | | |
|---|---|---|
| 6,128,535 A | 10/2000 | Maarse |
| 6,132,384 A | 10/2000 | Christopherson et al. |
| 6,134,473 A | 10/2000 | Hemming et al. |
| 6,141,581 A | 10/2000 | Olson et al. |
| 6,147,680 A | 11/2000 | Tareev |
| 6,148,230 A | 11/2000 | KenKnight |
| 6,148,234 A | 11/2000 | Struble |
| 6,163,724 A | 12/2000 | Hemming et al. |
| 6,169,921 B1 | 1/2001 | KenKnight et al. |
| 6,175,766 B1 | 1/2001 | Bornzin et al. |
| 6,190,326 B1 | 2/2001 | McKinnon et al. |
| 6,192,275 B1 | 2/2001 | Zhu et al. |
| 6,221,011 B1 | 4/2001 | Bardy |
| 6,226,551 B1 | 5/2001 | Zhu et al. |
| 6,227,072 B1 | 5/2001 | Ritchey et al. |
| 6,238,419 B1 | 5/2001 | Lindgren |
| 6,251,126 B1 | 6/2001 | Ottenhoff et al. |
| 6,253,102 B1 | 6/2001 | Hsu et al. |
| 6,258,039 B1 | 7/2001 | Okamoto et al. |
| 6,259,947 B1 | 7/2001 | Olson et al. |
| 6,266,554 B1 | 7/2001 | Hsu et al. |
| 6,270,457 B1 | 8/2001 | Bardy |
| 6,272,377 B1 | 8/2001 | Sweeney et al. |
| 6,275,731 B1 | 8/2001 | Zhu et al. |
| 6,277,072 B1 | 8/2001 | Bardy |
| 6,280,380 B1 | 8/2001 | Bardy |
| 6,280,462 B1 | 8/2001 | Hauser et al. |
| 6,282,440 B1 | 8/2001 | Brodnick et al. |
| 6,285,907 B1 | 9/2001 | Kramer et al. |
| 6,299,581 B1 | 10/2001 | Rapoport et al. |
| 6,312,378 B1 | 11/2001 | Bardy |
| 6,312,388 B1 | 11/2001 | Marcovecchio et al. |
| 6,324,421 B1 | 11/2001 | Stadler et al. |
| 6,324,427 B1 | 11/2001 | Florio |
| 6,336,903 B1 | 1/2002 | Bardy |
| 6,345,201 B1 | 2/2002 | Sloman et al. |
| 6,351,669 B1 | 2/2002 | Hartley et al. |
| 6,351,673 B1 | 2/2002 | Ding et al. |
| 6,353,759 B1 | 3/2002 | Hartley et al. |
| 6,358,203 B2 | 3/2002 | Bardy |
| 6,360,127 B1 | 3/2002 | Ding et al. |
| 6,363,270 B1 | 3/2002 | Colla et al. |
| 6,363,281 B1 | 3/2002 | Zhu et al. |
| 6,368,284 B1 | 4/2002 | Bardy |
| 6,368,287 B1 | 4/2002 | Hadas |
| 6,371,922 B1 | 4/2002 | Baumann et al. |
| 6,375,621 B1 | 4/2002 | Sullivan |
| 6,393,316 B1 | 5/2002 | Gillberg et al. |
| 6,398,728 B1 | 6/2002 | Bardy |
| 6,409,675 B1 | 6/2002 | Turcott |
| 6,411,848 B2 | 6/2002 | Kramer et al. |
| 6,415,174 B1 | 7/2002 | Bebehani et al. |
| 6,415,183 B1 | 7/2002 | Scheiner et al. |
| 6,418,340 B1 | 7/2002 | Conley et al. |
| 6,418,343 B1 | 7/2002 | Zhang et al. |
| 6,424,234 B1 | 7/2002 | Stevenson |
| 6,424,865 B1 | 7/2002 | Ding |
| 6,434,417 B1 | 8/2002 | Lovett |
| 6,434,428 B1 | 8/2002 | Sloman et al. |
| 6,438,409 B1 | 8/2002 | Malik et al. |
| 6,438,410 B2 | 8/2002 | Hsu et al. |
| 6,440,066 B1 | 8/2002 | Bardy |
| 6,449,503 B1 | 9/2002 | Hsu |
| 6,456,481 B1 | 9/2002 | Stevenson |
| 6,456,880 B1 | 9/2002 | Park et al. |
| 6,456,881 B1 | 9/2002 | Bornzin et al. |
| 6,459,929 B1 | 10/2002 | Hopper et al. |
| 6,466,820 B1 | 10/2002 | Juran et al. |
| 6,477,422 B1 | 11/2002 | Splett |
| 6,480,733 B1 | 11/2002 | Turcott |
| 6,480,734 B1 | 11/2002 | Zhang et al. |
| 6,487,443 B2 | 11/2002 | Olson et al. |
| 6,491,639 B1 | 12/2002 | Turcott |
| 6,493,586 B1 | 12/2002 | Stahmann et al. |
| 6,496,715 B1 | 12/2002 | Lee et al. |
| 6,505,067 B1 | 1/2003 | Lee et al. |
| 6,505,071 B1 | 1/2003 | Zhu et al. |
| 6,512,940 B1 | 1/2003 | Brabec et al. |
| 6,512,953 B2 | 1/2003 | Florio et al. |
| 6,522,915 B1 | 2/2003 | Ceballos et al. |
| 6,542,775 B2 | 4/2003 | Ding et al. |
| 6,553,259 B2 | 4/2003 | Mouchawar et al. |
| 6,564,106 B2 | 5/2003 | Guck et al. |
| 6,567,701 B2 | 5/2003 | Vonk |
| 6,574,507 B1 | 6/2003 | Bonnet |
| 6,589,188 B1 | 7/2003 | Street et al. |
| 6,595,927 B2 | 7/2003 | Pitts-Crick et al. |
| 6,597,951 B2 | 7/2003 | Kramer et al. |
| 6,600,949 B1 | 7/2003 | Turcott |
| 6,607,509 B2 | 8/2003 | Bobroff et al. |
| 6,611,712 B2 | 8/2003 | Spinelli et al. |
| 6,615,082 B1 | 9/2003 | Mandell |
| 6,615,083 B2 | 9/2003 | Kupper |
| 6,615,089 B1 | 9/2003 | Russie et al. |
| 6,618,619 B1 | 9/2003 | Florio et al. |
| 6,622,046 B2 | 9/2003 | Fraley et al. |
| 6,631,290 B1 | 10/2003 | Guck et al. |
| 6,640,136 B1 | 10/2003 | Helland et al. |
| 6,641,542 B2 | 11/2003 | Cho et al. |
| 6,654,637 B2 | 11/2003 | Rouw et al. |
| 6,658,293 B2 | 12/2003 | Vonk |
| 6,684,100 B1 | 1/2004 | Sweeney et al. |
| 6,690,967 B2 | 2/2004 | Meij |
| 6,701,170 B2 | 3/2004 | Stetson |
| 6,708,058 B2 | 3/2004 | Kim et al. |
| 6,725,085 B2 | 4/2004 | Schwartzmann et al. |
| 6,731,973 B2 | 5/2004 | Voith |
| 6,731,983 B2 | 5/2004 | Ericksen et al. |
| 6,731,984 B2 | 5/2004 | Cho et al. |
| 6,731,985 B2 | 5/2004 | Poore et al. |
| 6,738,668 B1 | 5/2004 | Mouchawar et al. |
| 6,738,669 B1 | 5/2004 | Sloman et al. |
| 6,754,523 B2 | 6/2004 | Toole |
| 6,754,528 B2 | 6/2004 | Bardy et al. |
| 6,760,615 B2 | 7/2004 | Ferek-Petric |
| 6,766,190 B2 | 7/2004 | Ferek-Petric |
| 6,768,923 B2 | 7/2004 | Ding et al. |
| 6,768,924 B2 | 7/2004 | Ding et al. |
| 6,772,008 B2 | 8/2004 | Zhu et al. |
| 6,773,404 B2 | 8/2004 | Poezevera et al. |
| 6,778,860 B2 | 8/2004 | Ostroff et al. |
| 6,782,291 B1 | 8/2004 | Bornzin et al. |
| 6,788,974 B2 | 9/2004 | Bardy et al. |
| 6,830,548 B2 | 12/2004 | Bonnet et al. |
| 6,834,204 B2 | 12/2004 | Ostroff et al. |
| 6,856,835 B2 | 2/2005 | Bardy et al. |
| 6,865,417 B2 | 3/2005 | Rissmann et al. |
| 6,866,044 B2 | 3/2005 | Bardy et al. |
| 6,881,192 B1 | 4/2005 | Park |
| 6,884,218 B2 | 4/2005 | Olson et al. |
| 6,885,893 B1 | 4/2005 | Lu |
| 6,888,538 B2 | 5/2005 | Ely et al. |
| 6,889,079 B2 | 5/2005 | Bocek et al. |
| 6,890,306 B2 | 5/2005 | Poezevera |
| 6,895,274 B2 | 5/2005 | Mower |
| 6,904,315 B2 | 6/2005 | Panken et al. |
| 6,904,320 B2 | 6/2005 | Park et al. |
| 6,915,160 B2 | 7/2005 | Auricchio et al. |
| 6,915,164 B2 | 7/2005 | Bradley et al. |
| 6,917,832 B2 | 7/2005 | Hutten et al. |
| 6,925,324 B2 | 8/2005 | Shusterman |
| 6,925,330 B2 | 8/2005 | Kleine |
| 6,927,721 B2 | 8/2005 | Ostroff |
| 6,928,324 B2 | 8/2005 | Park et al. |
| 6,937,907 B2 | 8/2005 | Bardy et al. |
| 6,944,495 B2 | 9/2005 | MacAdam et al. |
| 6,944,579 B2 | 9/2005 | Shimizu |
| 6,950,702 B2 | 9/2005 | Sweeney |
| 6,950,705 B2 | 9/2005 | Bardy et al. |
| 6,952,608 B2 | 10/2005 | Ostroff |
| 6,952,610 B2 | 10/2005 | Ostroff |
| 6,954,670 B2 | 10/2005 | Ostroff |
| 6,959,214 B2 | 10/2005 | Pape et al. |
| 6,961,613 B2 | 11/2005 | Bjorling et al. |

(56) References Cited

U.S. PATENT DOCUMENTS

| | | |
|---|---|---|
| 6,961,619 B2 | 11/2005 | Casey |
| 6,973,350 B1 | 12/2005 | Levine et al. |
| 6,975,904 B1 | 12/2005 | Sloman |
| 6,978,178 B2 | 12/2005 | Sommer et al. |
| 6,983,264 B2 | 1/2006 | Shimizu |
| 6,988,003 B2 | 1/2006 | Bardy et al. |
| 6,993,379 B1 | 1/2006 | Kroll et al. |
| 6,993,389 B2 | 1/2006 | Ding et al. |
| 6,999,817 B2 | 2/2006 | Park et al. |
| 7,006,869 B2 | 2/2006 | Bradley |
| 7,025,730 B2 | 4/2006 | Cho et al. |
| 7,027,861 B2 | 4/2006 | Thompson |
| 7,027,868 B2 | 4/2006 | Rueter et al. |
| 7,027,871 B2 | 4/2006 | Burnes et al. |
| 7,031,773 B1 | 4/2006 | Levine et al. |
| 7,039,459 B2 | 5/2006 | Bardy |
| 7,039,465 B2 | 5/2006 | Bardy |
| 7,043,299 B2 | 5/2006 | Erlinger |
| 7,050,851 B2 | 5/2006 | Plombon et al. |
| 7,062,327 B2 | 6/2006 | Bradley et al. |
| 7,065,400 B2 | 6/2006 | Schechter |
| 7,065,407 B2 | 6/2006 | Bardy |
| 7,065,410 B2 | 6/2006 | Bardy et al. |
| 7,069,080 B2 | 6/2006 | Bardy |
| 7,076,296 B2 | 7/2006 | Rissmann et al. |
| 7,079,988 B2 | 7/2006 | Albera |
| 7,081,095 B2 | 7/2006 | Lynn et al. |
| 7,085,599 B2 | 8/2006 | Kim et al. |
| 7,090,682 B2 | 8/2006 | Sanders et al. |
| 7,092,754 B2 | 8/2006 | Bardy et al. |
| 7,094,207 B1 | 8/2006 | Koh |
| 7,096,064 B2 | 8/2006 | Deno et al. |
| 7,103,404 B2 | 9/2006 | Staler et al. |
| 7,107,093 B2 | 9/2006 | Burnes |
| 7,113,823 B2 | 9/2006 | Yonce et al. |
| 7,115,097 B2 | 10/2006 | Johnson |
| 7,117,036 B2 | 10/2006 | Florio |
| 7,120,495 B2 | 10/2006 | Bardy et al. |
| 7,123,960 B2 | 10/2006 | Ding |
| 7,127,290 B2 | 10/2006 | Girouard et al. |
| 7,129,935 B2 | 10/2006 | Mackey |
| 7,139,610 B2 | 11/2006 | Ferek-Petric |
| 7,144,586 B2 | 12/2006 | Levy et al. |
| 7,146,212 B2 | 12/2006 | Bardy et al. |
| 7,149,575 B2 | 12/2006 | Ostroff et al. |
| 7,155,278 B2 | 12/2006 | King et al. |
| 7,160,252 B2 | 1/2007 | Cho et al. |
| 7,177,689 B2 | 2/2007 | Ternes et al. |
| 7,179,229 B1 | 2/2007 | Koh |
| 7,181,285 B2 | 2/2007 | Lindh |
| 7,184,835 B2 | 2/2007 | Kramer et al. |
| 7,191,003 B2 | 3/2007 | Greenhut et al. |
| 7,191,004 B2 | 3/2007 | Kim et al. |
| 7,194,302 B2 | 3/2007 | Bardy et al. |
| 7,194,309 B2 | 3/2007 | Ostroff et al. |
| 7,194,313 B2 | 3/2007 | Libbus |
| 7,203,540 B2 | 4/2007 | Ding et al. |
| 7,203,542 B2 | 4/2007 | Obel |
| 7,203,543 B2 | 4/2007 | Meyer et al. |
| 7,212,862 B2 | 5/2007 | Park et al |
| 7,225,021 B1 | 5/2007 | Park et al. |
| 7,228,173 B2 | 6/2007 | Cazares |
| 7,233,821 B2 | 6/2007 | Hettrick et al. |
| 7,236,819 B2 | 6/2007 | Brockway |
| 7,242,978 B2 | 7/2007 | Cao |
| 7,245,962 B2 | 7/2007 | Ciaccio et al. |
| 7,248,921 B2 | 7/2007 | Palreddy et al. |
| 7,248,925 B2 | 7/2007 | Bruhns et al. |
| 7,263,399 B2 | 8/2007 | Carlson |
| 7,277,754 B2 | 10/2007 | McCabe et al. |
| 7,286,876 B2 | 10/2007 | Yonce et al. |
| 7,299,086 B2 | 11/2007 | McCabe et al. |
| 7,299,093 B2 | 11/2007 | Zhu et al. |
| 7,308,311 B2 | 12/2007 | Sorensen et al. |
| 7,319,900 B2 | 1/2008 | Kim et al. |
| 7,330,761 B2 | 2/2008 | Zhang |
| 7,337,000 B2 | 2/2008 | Meyer et al. |
| 7,359,749 B2 | 4/2008 | Quenet et al. |
| 7,369,889 B2 | 5/2008 | Astrom et al. |
| 7,392,086 B2 | 6/2008 | Sathaye |
| 7,426,412 B1 | 9/2008 | Schecter |
| 7,438,686 B2 | 10/2008 | Cho et al. |
| 7,457,664 B2 | 11/2008 | Zhang et al. |
| 7,463,924 B2 | 12/2008 | Bardy et al. |
| 7,468,040 B2 | 12/2008 | Hartley et al. |
| 7,477,932 B2 | 1/2009 | Lee et al. |
| 7,499,751 B2 | 3/2009 | Meyer et al. |
| 7,509,170 B2 | 3/2009 | Zhang et al. |
| 7,519,423 B2 | 4/2009 | Begemann et al. |
| 7,558,628 B2 | 7/2009 | Yonce et al. |
| 7,580,741 B2 | 8/2009 | Cazares et al. |
| 7,587,240 B2 | 9/2009 | Zhang et al. |
| 7,617,002 B2 | 11/2009 | Goetz |
| 7,647,108 B2 | 1/2010 | Freeberg |
| 7,653,431 B2 | 1/2010 | Cazares et al. |
| 7,680,536 B2 | 3/2010 | Sathaye et al. |
| 7,684,861 B2 | 3/2010 | Sanders |
| 7,706,866 B2 | 4/2010 | Zhang et al. |
| 7,734,347 B2 | 6/2010 | Sathaye et al. |
| 7,738,959 B2 | 6/2010 | Manrodt et al. |
| 7,761,162 B2 | 7/2010 | Dong et al. |
| 7,774,064 B2 * | 8/2010 | Meyer et al. .............. 607/28 |
| 8,145,310 B2 * | 3/2012 | Dong et al. .............. 607/27 |
| 2001/0049542 A1 | 12/2001 | Florio et al. |
| 2002/0002327 A1 | 1/2002 | Grant et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035381 A1 | 3/2002 | Bardy et al. |
| 2002/0052631 A1 | 5/2002 | Sullivan et al. |
| 2002/0082658 A1 | 6/2002 | Heinrich et al. |
| 2002/0095184 A1 | 7/2002 | Bardy et al. |
| 2002/0095188 A1 | 7/2002 | Mower |
| 2002/0107544 A1 | 8/2002 | Ostroff et al. |
| 2002/0107545 A1 | 8/2002 | Rissmann et al. |
| 2002/0138111 A1 | 9/2002 | Greenhut et al. |
| 2002/0143264 A1 | 10/2002 | Ding et al. |
| 2002/0183795 A1 | 12/2002 | Rouw et al. |
| 2002/0183798 A1 | 12/2002 | Vonk |
| 2002/0188211 A1 | 12/2002 | Voith |
| 2003/0023175 A1 | 1/2003 | Arzbaecher et al. |
| 2003/0050671 A1 | 3/2003 | Bradley |
| 2003/0083708 A1 | 5/2003 | Bradley et al. |
| 2003/0083710 A1 | 5/2003 | Ternes et al. |
| 2003/0083711 A1 | 5/2003 | Yonce et al. |
| 2003/0125777 A1 | 7/2003 | Ding et al. |
| 2003/0135248 A1 | 7/2003 | Stypulkowski |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0208241 A1 | 11/2003 | Bradley et al. |
| 2003/0212436 A1 | 11/2003 | Brown |
| 2004/0064162 A1 | 4/2004 | Manrodt et al. |
| 2004/0082975 A1 | 4/2004 | Meyer et al. |
| 2004/0116971 A1 | 6/2004 | Bjorling et al. |
| 2004/0116978 A1 | 6/2004 | Bradley |
| 2004/0127805 A1 | 7/2004 | MacAdam et al. |
| 2004/0127950 A1 | 7/2004 | Kim et al. |
| 2004/0133248 A1 | 7/2004 | Frei et al. |
| 2004/0171959 A1 | 9/2004 | Stadler et al. |
| 2004/0172065 A1 | 9/2004 | Sih et al. |
| 2004/0215253 A1 | 10/2004 | Weinberg |
| 2004/0215277 A1 | 10/2004 | Oosterhoff et al. |
| 2004/0230229 A1 | 11/2004 | Lovett et al. |
| 2004/0243014 A1 | 12/2004 | Lee et al. |
| 2004/0260351 A1 | 12/2004 | Holmstrom et al. |
| 2005/0004612 A1 | 1/2005 | Scholten et al. |
| 2005/0010120 A1 | 1/2005 | Jung |
| 2005/0038478 A1 | 2/2005 | Klepfer et al. |
| 2005/0043652 A1 | 2/2005 | Lovett et al. |
| 2005/0060002 A1 | 3/2005 | Zhu et al. |
| 2005/0060007 A1 | 3/2005 | Goetz |
| 2005/0065587 A1 | 3/2005 | Gruzwa |
| 2005/0085865 A1 | 4/2005 | Tehrani |

(56) References Cited

U.S. PATENT DOCUMENTS

| | | |
|---|---|---|
| 2005/0113710 A1 | 5/2005 | Stahmann et al. |
| 2005/0131476 A1 | 6/2005 | Kim et al. |
| 2005/0131477 A1 | 6/2005 | Meyer et al. |
| 2005/0131478 A1 | 6/2005 | Kim et al. |
| 2005/0143785 A1 | 6/2005 | Libbus |
| 2005/0288600 A1 | 12/2005 | Zhang et al. |
| 2006/0069322 A1 | 3/2006 | Zhang et al. |
| 2006/0074331 A1 | 4/2006 | Kim et al. |
| 2006/0074454 A1 | 4/2006 | Freeberg |
| 2006/0111747 A1 | 5/2006 | Cazares et al. |
| 2006/0116593 A1 | 6/2006 | Zhang et al. |
| 2006/0129193 A1 | 6/2006 | Zhang |
| 2006/0129194 A1 | 6/2006 | Zhang |
| 2006/0129195 A1 | 6/2006 | Sathaye et al. |
| 2006/0129196 A1 | 6/2006 | Dong et al. |
| 2006/0129197 A1 | 6/2006 | Zhang et al. |
| 2006/0129198 A1 | 6/2006 | Zhang et al. |
| 2006/0129199 A1 | 6/2006 | Zhang et al. |
| 2006/0241706 A1 | 10/2006 | Yonce et al. |
| 2006/0241711 A1 | 10/2006 | Sathaye |
| 2006/0247693 A1 | 11/2006 | Dong et al. |
| 2006/0247695 A1 | 11/2006 | Stalsberg et al. |
| 2006/0253043 A1 | 11/2006 | Zhang et al. |
| 2006/0253044 A1 | 11/2006 | Zhang et al. |
| 2007/0049974 A1 | 3/2007 | Li et al. |
| 2007/0055124 A1 | 3/2007 | Viswanathan et al. |
| 2007/0142737 A1 | 6/2007 | Cazares et al. |
| 2007/0142741 A1 | 6/2007 | Berthon-Jones et al. |
| 2007/0239057 A1 | 10/2007 | Pu et al. |
| 2007/0255321 A1 | 11/2007 | Gerber et al. |
| 2008/0004665 A1 | 1/2008 | McCabe et al. |
| 2008/0009909 A1 | 1/2008 | Sathaye et al. |
| 2008/0045851 A1 | 2/2008 | Cazares et al. |
| 2008/0046019 A1 | 2/2008 | Sathaye et al. |
| 2008/0071318 A1 | 3/2008 | Brooke et al. |
| 2008/0234556 A1 | 9/2008 | Brooke et al. |
| 2008/0275522 A1 | 11/2008 | Dong |
| 2008/0294215 A1 | 11/2008 | Sathaye |
| 2008/0300644 A1 | 12/2008 | Sathaye |
| 2009/0030470 A1 | 1/2009 | Holmstrom |
| 2009/0043351 A1 | 2/2009 | Sathaye et al. |
| 2009/0043352 A1 | 2/2009 | Brooke |
| 2009/0210024 A1 | 8/2009 | M. |

FOREIGN PATENT DOCUMENTS

| | | |
|---|---|---|
| EP | 0940155 | 9/1999 |
| EP | 1038498 | 9/2000 |
| EP | 1151718 | 11/2001 |
| EP | 1291038 | 3/2003 |
| EP | 1629863 | 3/2006 |
| WO | WO 92/17240 | 10/1992 |
| WO | WO 92/20402 | 11/1992 |
| WO | WO 99/04841 | 4/1999 |
| WO | WO 00/01438 | 1/2000 |
| WO | WO 00/17615 | 3/2000 |
| WO | WO 02/40097 | 5/2002 |
| WO | WO 02/47761 | 6/2002 |
| WO | WO 02/087696 | 11/2002 |
| WO | WO 03/003905 | 1/2003 |
| WO | WO 03/028550 | 4/2003 |
| WO | WO 2004/026398 | 4/2004 |
| WO | WO 2004/091720 | 10/2004 |
| WO | WO 2005/058412 | 6/2005 |
| WO | WO 2005/089865 | 9/2005 |
| WO | WO 2006/065707 | 6/2006 |
| WO | WO 2007/087025 | 8/2007 |
| WO | WO 2008/005270 | 1/2008 |
| WO | WO 2009/020639 | 2/2009 |

OTHER PUBLICATIONS

Ajilore et al., "Nightcap: Laboratory and home-based evaluation of a portable sleep monitor," 32 *Psychophysiology*, 32-98 (1995). Abstract only.

Belouchrani et al., "Blind Source Separation Based on Time-Frequency Signal Representations," *IEEE Transactions on Signal Processing*, vol. 46, No. 11, pp. 2888-2897, Nov. 1998.

Cohen et al., "Capture Management Efficacy in children and young adults with endocardial and unipolar epicardial systems." *Europace*, vol. 6, pp. 248-255 (2004).

Comon, "Independent component analysis, a new concept?" *Signal Processing*, vol. 36, No. 3, pp. 287-314, Apr. 1994.

Gallois et al., "Multi-Channel Analysis of the EEG Signals and Statistic Particularities for Epileptic Seizure Forecast," *Second Joint EMBS/BMES Conference*, pp. 208-215, Oct. 23-26, 2002.

Gradaus et al., "Nonthoracotomy Implantable Cardioverter Defibrillator Placement in Children: Use of a Subcutaneous Array Leads and Abdominally Placed Implantable Cardioverter Defibrillators in Children," *Journal of Cardiovascular Electrophysiology*, vol. 12, No. 3, pp. 356-360, Mar. 2001.

Hartz et al., "New Approach to Defibrillator Insertion," *Journal of Thoracic Cardiovascular Surgery*, vol. 97, pp. 920-922 (1989).

Hyvärinen et al., "Independent Component Analysis: a Tutorial," *Helsinski University of Technology*, Apr. 1999.

Kolettis et al., "Submammary Implantation of a Cardioverter-Defibrillator with a Nonthoractomy Lead System," *American Heart Journal*, vol. 126, pp. 1222-1223, Nov. 1993.

Krahn et al., "Recurrent syncope. Experience with an implantable loop record," *Cardiol. Clin.*, vol.15(2), pp. 316-326, May 1997.

Leng et al., "Lead Configuration for Defibrillator Implantation in a Patient with Congenital Heart Disease and a Mechanical Prosthetic Tricuspid Valve", *PACE*, vol. 24, No. 8, pp. 1291-1292, Aug. 2001.

Park et al., "Use of an Implantable Cardioverter Defibrillator in an Eight-Month-Old Infant with Ventricular Fibrillation Arising from a Myocardial Fibroma," *PACE*, vol. 22, No. 1, pp. 138-139, Jan. 1999.

Rieta, et al., "Atrial Activity Extraction Based on Blind Source Separation as an Alternative to QRST Cancellation for Atrial Fibrillation Analysis," *Computers in Cardiology*, vol. 27, pp. 69-72 (2000).

Schuder et al., "Experimental Ventricular Defibrillation with an Automatic and Completely Implanted System," *Trans. American Society Artif Int. Organs*, vol. 16, pp. 207-212 (1970).

Schuder et al., "Transthoracic Ventricular Defibrillation in the Dog with Truncated and Untruncated Exponential Stimuli," *IEEE Transitions on Bio-Medical Engineering*, vol. BME-18, No. 6, pp. 410-415, Nov. 1971.

Schuder et al., "Ventricular Defibrillation in the Dog Using Implanted and Partially Implanted Electrode Systems," *American Journal of Cardiology*, vol. 33, pp. 243-247, Feb. 1974.

Smits et al., "Defibrillation Threshold (DFT) Model of a Fully Subcutaneous ICD System," *Europace Supplements*, vol. 2, Jun. 2001 at col. 778, p. B83.

Splett et al., "Determination of Pacing Capture in Implantable Defibrillators Benefit of Evoked Response Detection Using RV Coil to Can Vector", *PACE*, vol. 23 (2000) pp. 1645-1650.

Stirbis et al., "Optimizing of the Shape of Implanted Artificial Pacemakers," *Kaunas Medical Institute*, Translated from *Meditsinskaya Tekhnika*, No. 6, pp. 25-27 (1986).

Verrier et al., "Sleep, dreams, and sudden death: the case for sleep as an autonomic stress test for the heart," *31 Cardiovascular Research*, 181-211 (1996).

Verrier et al., "Sleep Related Cardiovascular Risk: New Home-Based Monitoring Technology for Improved Diagnosis and Therapy," *2 A.N.E.*, 158-175 (1997).

Waldemark et al., "Detection of Apnea using Short Window FFT Technique and Artificial Neural Network," 3390 *SPIE International Society for Optical Engineering*, 122-133 (1998). Partial article.

Zarzoso et al., "Blind Separation of Independent Sources for Virtually Any Source Probability Density Function," *IEEE Transactions on Signal Processing*, vol. 47, No. 9, pp. 2419-2432, Sep. 1999.

Zarzoso et al., "Noninvasive Fetal Electrocardiogram Extraction: Blind Separation Versus Adaptive Noise Cancellation," *IEEE Transactions on Biomedical Engineering*, vol. 48, No. 1, pp. 12-18, Jan. 2001.

* cited by examiner

NON-CAPTURED INTRINSIC DISCRIMINATION IN CARDIAC PACING RESPONSE CLASSIFICATION

RELATED APPLICATIONS

This application is a continuation of U.S. application Ser. No. 12/217,652, filed on Jul. 8, 2008, now U.S. Pat. No. 8,145,310, which is a continuation of U.S. application Ser. No. 11/116,558, filed on Apr. 28, 2005, now abandoned; and is a continuation-in-part of U.S. application Ser. No. 12/008,876, filed on Jan. 15, 2008, now U.S. Pat. No. 8,831,726, which is a continuation of U.S. application Ser. No. 10/733,869, filed on Dec. 11, 2003, now U.S. Pat. No. 7,319,900, the entire disclosures of which are all hereby incorporated herein by reference.

FIELD OF THE INVENTION

The present invention relates generally to implantable medical devices and, more particularly, to cardiac devices and methods that discriminate non-captured intrinsic beats during evoked response detection.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically include circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal preceding the contraction is denoted the captured response (CR). The captured response typically includes an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Detecting if a pacing pulse "captures" the heart and produces a contraction allows the cardiac rhythm management system to adjust the energy level of pace pulses to correspond to the optimum energy expenditure that reliably produces capture. Further, capture detection allows the cardiac rhythm management system to initiate a back-up pulse at a higher energy level whenever a pace pulse does not produce a contraction.

A fusion beat is a cardiac contraction that occurs when two cardiac depolarizations of a particular chamber, but from separate initiation sites, merge. At times, a depolarization initiated by a pacing pulse may merge with an intrinsic beat, producing a fusion beat. Fusion beats, as seen on electrocardiographic recordings, exhibit various morphologies. The merging depolarizations of a fusion beat do not contribute evenly to the total depolarization.

Pseudofusion occurs when a pacing stimulus is delivered on a spontaneous P wave during atrial pacing or on a spontaneous QRS complex during ventricular pacing. In pseudofusion, the pacing stimulus may be ineffective because the tissue around the electrode has already spontaneously depolarized and is in its refractory period.

Noise presents a problem in evoked response detection processes when the pacemaker mistakenly identifies noise as capture, fusion/pseudofusion, or intrinsic activity. Noise mistakenly identified as capture or fusion/pseudofusion may cause a pacemaker to erroneously withhold backup pacing under loss of capture conditions. Noise mistakenly identified as non-captured intrinsic activity may lead to a premature loss of capture determination during threshold testing.

In the event that the pace does not capture the heart and capture or fusion/pseudofusion would then not occur, intrinsic activity may occur early enough in the cardiac cycle to appear as an evoked response when the pace did not actually capture the heart. These non-captured intrinsic beats represent a loss of capture. The misclassification of non-captured intrinsic beats as capture or fusion beats may result in low threshold measurement during threshold testing.

SUMMARY OF THE INVENTION

The present invention involves various cardiac devices and methods that discriminate non-captured intrinsic beats during evoked response detection and classification. An embodiment of a method of classifying a cardiac response to a pacing pulse in accordance with the present invention involves delivering a pacing pulse to a heart and sensing a cardiac signal following delivery of the pacing pulse. The cardiac response to the pacing pulse is classified as a non-captured intrinsic beat based on one or more characteristics of the cardiac signal. Classifying the cardiac response may involve detecting one or both of a peak time and peak amplitude of the cardiac signal, and may be based on one or both of the peak time and peak amplitude.

Other embodiments of methods of classifying a cardiac response to a pacing pulse in accordance with the present invention involve sensing for a cardiac signal peak in at least one intrinsic beat detection window associated with an intrinsic beat amplitude range and an intrinsic beat time interval. The cardiac response may be classified as a non-captured intrinsic beat if the cardiac signal peak is detected in at least one intrinsic beat detection window. Methods may further involve sensing for a cardiac signal peak in at least two capture detection windows, each associated with a captured response amplitude range and a captured response time interval. The cardiac response may be classified as a captured response if the cardiac signal peaks are detected in at least two capture detection windows. Further, the cardiac response may be classified as fusion if the cardiac signal peak is not detected in at least one capture detection window, and the cardiac signal peak is not detected in the at least one intrinsic detection window.

Other embodiments of a method of classifying a cardiac response to a pacing pulse in accordance with the present invention involve sensing for the cardiac signal peak in at least one noise detection window associated with a noise window amplitude range and a noise window time interval. The cardiac response may be classified as an unknown cardiac signal behavior if the cardiac signal peak is detected in the at least one noise detection window.

Further embodiments in accordance with the present invention are directed to systems for classifying a cardiac response to a pacing pulse. Systems in accordance with the present invention may include a sensor system configured to sense a cardiac signal following delivery of the pacing pulse with a processor coupled to the sensing system. The processor may be configured to detect one or more features of the cardiac signal and to classify the cardiac response to the pacing pulse as a non-captured intrinsic beat based on the one or more cardiac signal features. The processor may be configured to detect one or more peak times and/or amplitudes of the cardiac signal and to classify the cardiac response based on the peak time(s) and/or amplitude(s). The processor may discriminate the non-captured intrinsic beat from other cardiac activity based on the one or more features of the cardiac signal. The processor may classify the cardiac response as the non-captured intrinsic beat if a feature value associated with a particular cardiac signal feature is consistent with an expected feature value associated with a non-captured intrinsic beat.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
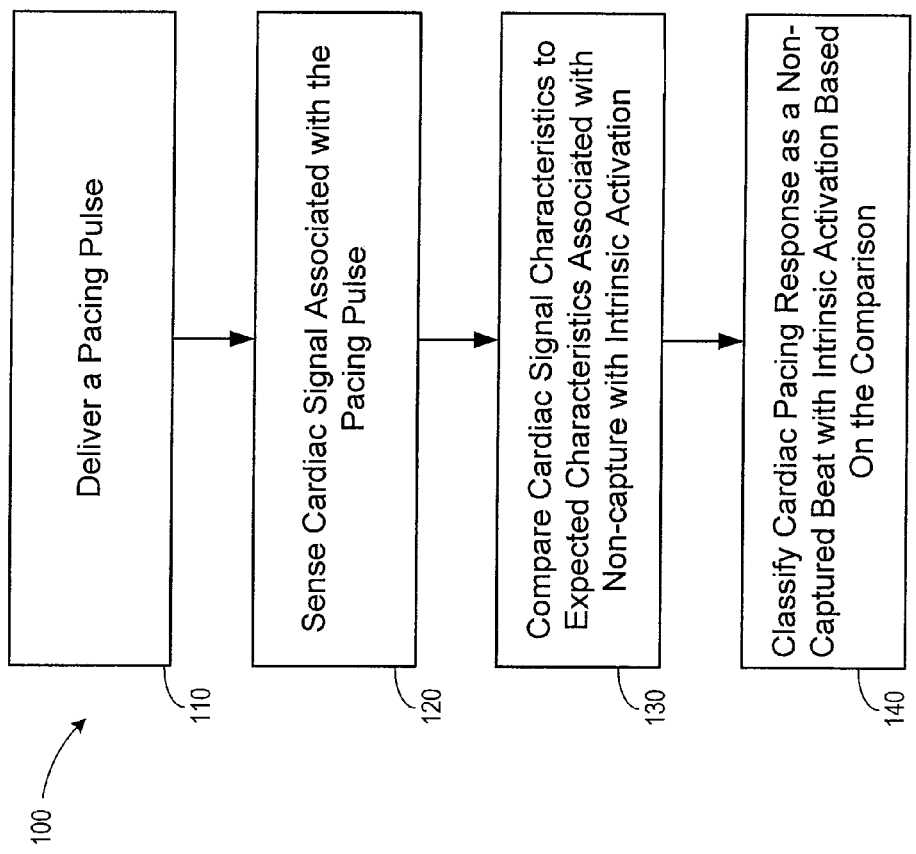
FIG. 1 is a flowchart of a method that discriminates non-captured intrinsic beats during evoked response detection and classification in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Cardiac response classification may be implemented by a pacemaker or other cardiac rhythm management (CRM) device to determine whether an applied electrical pacing stimulus captures the heart. Embodiments of the invention are directed to cardiac devices and methods that discriminate non-captured intrinsic beats during cardiac pacing response determination. The methods described herein use one or more characteristics of the cardiac signal, e.g., cardiac signal features, samples, discrete and/or analog morphological waveform characteristics, to discriminate between various responses to pacing and may be used during automatic capture verification or capture threshold testing.

Cardiac pacing responses may include, for example, non-capture, capture, fusion/pseudofusion, and noncapture with intrinsic activity.

Processes for recognizing the cardiac response to pacing may rely on one or more templates characterizing various types of possible responses. The system may compare a cardiac signal sensed after delivery of the pacing pulse to the templates. If the cardiac signal is sufficiently similar to a particular template, then the cardiac response may be classified as the type of response characterized by the template.

In some embodiments, a template characterizing a particular type of cardiac pacing response may comprise one or more detection windows that represent an expected range of values of a cardiac signal associated with a particular type of cardiac response. For example, if the cardiac signal following the pacing pulse is detected within the detection regions, then the system classifies the cardiac response as the particular type of cardiac response characterized by the template.

Automatic threshold and automatic capture verification are algorithms that may be used by cardiac rhythm management (CRM) devices. These algorithms attempt to discriminate captured beats from non-captured beats. Detection of non-capture may be complicated by non-capture beats that include intrinsic activation. For some patients, for example, patients with intact AV conduction, a non-captured beat with intrinsic activation may have a morphology somewhat similar to a captured response. Thus, templates used to discriminate between a captured response and a noncaptured response with intrinsic activation must be formed and used accurately to discriminate between the two types of responses. In automatic threshold testing, erroneous classification of a noncaptured intrinsic beat as a captured response may cause the capture threshold to be incorrectly identified.

Embodiments of the present invention are directed to detection and classification of non-captured beats with intrinsic activation. Detection and classification of such beats may be accomplished by recognizing the characteristic signal features of such non-captured intrinsic beats. In accordance with one aspect of the invention, detection and classification of non-captured intrinsic beats is accomplished based on the determination of one or more features of the cardiac signal, for example, one or more peak amplitudes and associated peak times.

A template for recognizing the intrinsic beats may comprise one or more intrinsic detection windows, having dimensions of time and amplitude, into which peaks of the non-captured intrinsic signal are expected to fall. If the peaks of a sensed cardiac signal fall into one or more of the intrinsic detection windows, the cardiac response may be classified as a non-captured response with intrinsic activation. Methods and systems for generating and updating detection windows, aspects of which may be utilized in connection with the embodiments of the present invention are described in commonly owned U.S. Pat. Nos. 7,499,751 and 7,574,260, both of which are incorporated herein by reference.

One embodiment of the invention is based on the peak amplitude and timing of non-captured intrinsic activity, relative to those of captured beats. As will be described in more detail below, non-captured intrinsic beats typically have a relatively late peak relative to captured beats, while fusion beats typically have earlier peaks. Devices and methods in accordance with the present invention provide a non-captured intrinsic detection window after a capture detection window, to discriminate these non-captured intrinsic beats. In addition to the relatively late peak, an intrinsic beat may also have a larger peak amplitude when compared to the peak amplitude of a captured response. Therefore, embodiments of the present invention may include a second non-captured intrinsic detection window that may be used to discriminate non-captured intrinsic beats with increased peak amplitudes.

A further check may be performed to discriminate and manage unusual intrinsic beats, such as premature ventricular contraction (PVC). For example, one or more noise detection windows may also be provided in accordance with the present invention to detect a relatively large positive peak associated with PVC and uncommon to the other cardiac responses.

FIG. 1 is a flowchart of a method 100 of detecting non-captured beats with intrinsic activation in accordance with embodiments of the invention. Pacing pulses 110 are delivered to a patient's heart. For example, the pacing pulses may be delivered to one or more of a right ventricle, right atrium, left ventricle, and/or left atrium. Cardiac signals 120 following the pacing pulse that are associated with, or in response to, the pacing pulse are sensed, and measurements are made of one or more characteristics of the cardiac signal, such as cardiac signal features that may include amplitudes and timings associated with positive and/or negative cardiac signal peaks. The one or more cardiac signal characteristics are compared 130 to one or more expected characteristics associated with a non-captured response with intrinsic activation. If the one or more sensed cardiac signal characteristics are consistent with the one or more expected characteristics, the cardiac pacing response is classified 140 as a non-captured response with intrinsic activation.

Figure 2:
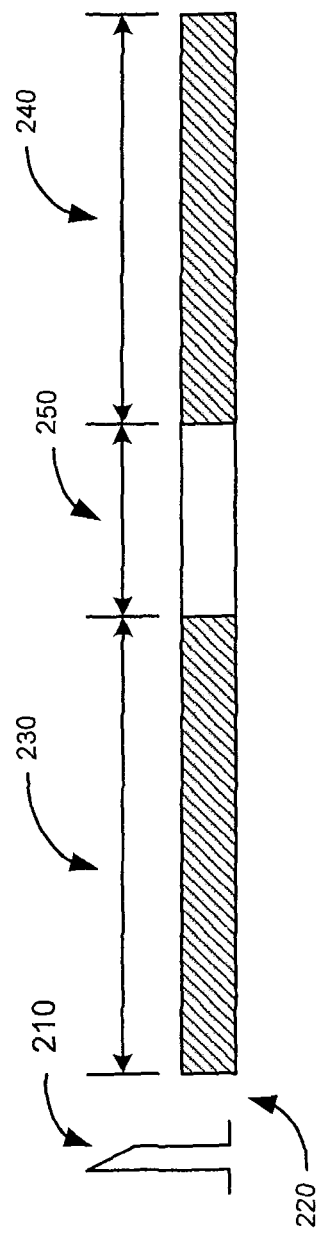
FIG. 2 is a diagram illustrating time intervals that may be used for discriminating non-captured intrinsic beats during evoked response detection and classification in accordance with embodiments of the invention.

FIG. 2 is a diagram illustrating multiple time intervals that may be used for discriminating non-captured intrinsic beats during cardiac pacing response classification in accordance with embodiments of the invention. A pacing stimulation 210 is delivered to the heart, for example, to the right ventricle. The cardiac signal is blanked for a period of time 220, typically about 0 milliseconds to about 40 milliseconds, following the delivery of the pacing stimulation 210. After the blanking period 220, a first time interval 230 is initiated. The duration of the first time interval 230 may be a programmable duration, for example, less than about 325 milliseconds. The cardiac signal associated with the pacing pulse is sensed during the first time interval 230. If the positive or negative amplitude of the cardiac signal does not exceed a threshold in the first time interval 230, then the cardiac response may be classified as a noncaptured response. If the cardiac signal exceeds the threshold value, then various features of the cardiac signal may be determined and used for cardiac pacing response classification. In some cases, sensing of the cardiac signal may be extended to additional time intervals, such as the second time interval 240. The second time interval 240 may be programmable, and may have a duration less than about 325 milliseconds. The durations of the additional time intervals may be different or the same as the duration of the first time interval.

A delay period 250 may be established between the end of one time interval 230 and the beginning of another time interval 240. The duration of the delay may be in a range of about 0 milliseconds (no delay) to about 40 milliseconds, for example. The cardiac response to the pacing stimulation 210 may be classified based on characteristics of the cardiac signal determined in the first and/or the additional time intervals 230, 240.

Figure 3:
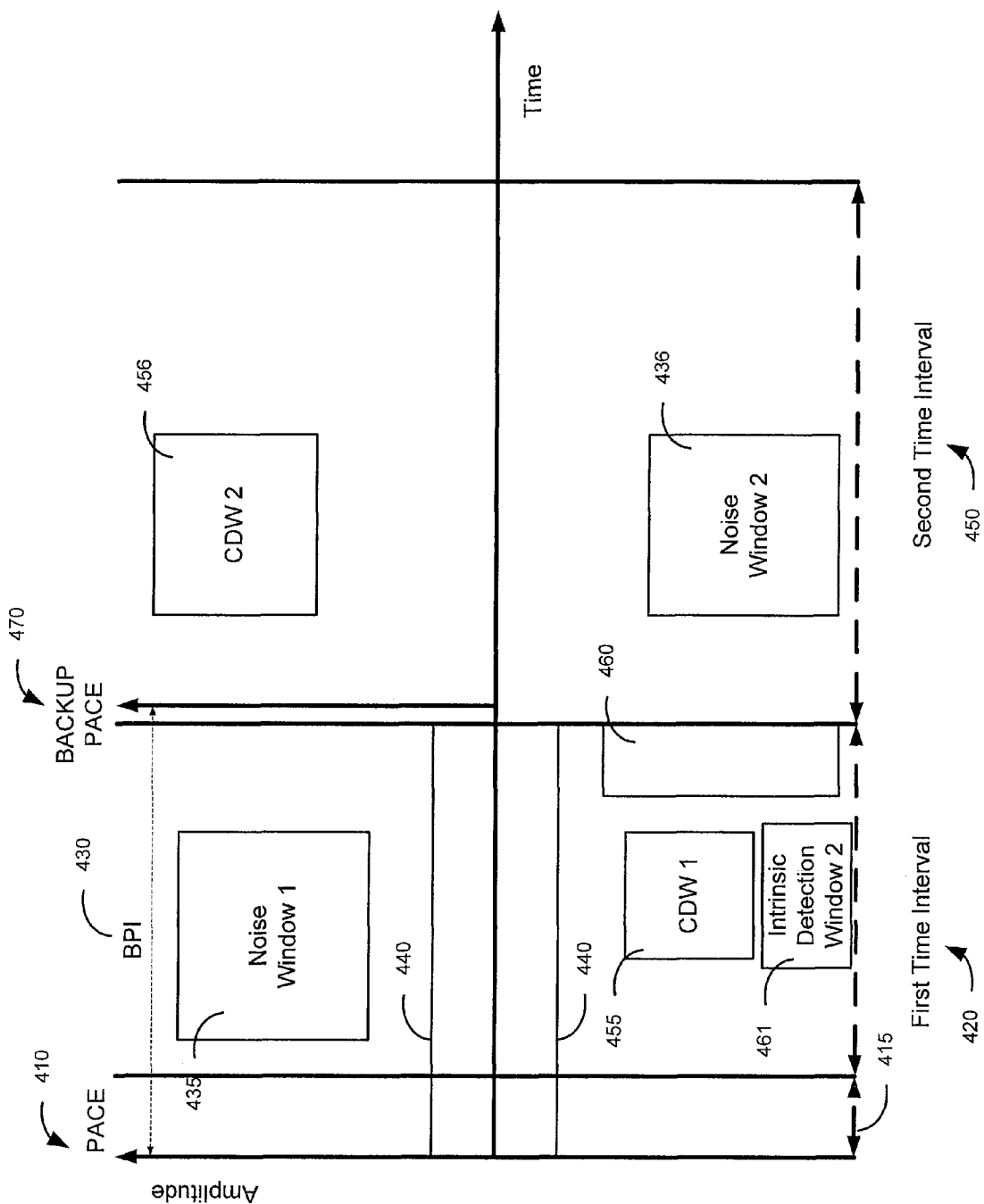
FIG. 3 is a graph including cardiac response classification windows and noise detection windows that may be utilized for cardiac devices and methods that discriminate non-captured intrinsic beats during evoked response detection and classification in accordance with embodiments of the invention.

FIG. 3 illustrates detection windows that may be utilized in cardiac devices and methods that discriminate non-captured intrinsic beats during cardiac pacing response classification in accordance with embodiments of the invention. Following delivery of a pace 410, the sensing system is blanked, e.g., the sense electrodes are disconnected from sense amplifiers or the sense amplifiers are rendered inoperative, during a blanking period 415. Following the blanking period, the cardiac signal is sensed in one or more time intervals. As illustrated in FIG. 3, sensing may occur in two time intervals 420, 450 following the pacing pulse 410. In some scenarios, the second 450 and subsequent time intervals (not shown) may be triggered by events occurring in one or more previous intervals.

In various implementations, sensing may be performed using the same electrode combination that was used to deliver the pacing stimulation. In other implementations, the pacing stimulation may be delivered using a first electrode configuration and sensing may use a second electrode configuration. Use of a sensing vector that is spatially removed from the pacing vector may be particularly useful for diminishing the effect of a pacing artifact on the cardiac signal following pacing. Systems and methods for classifying a cardiac response to pacing using multiple time intervals and various sensing and pacing vectors are described in commonly owned U.S. Pat. Nos. 7,319,910, and 7,774,064 and U.S. Publication No. 2005/0131478; which are hereby incorporated herein by reference.

During the first time interval 420, the system senses for a positive or negative cardiac signal amplitude beyond a threshold level 440. If the cardiac signal amplitude falls within the threshold 440 during the first time interval 420, then the cardiac response is classified as noncapture and a backup pace 470 may be delivered. The backup pace 470 is typically a high energy pace that is delivered following a backup interval (BPI) 430. For example, the BPI 430 may include an interval of about 100 ms timed from the delivery of the primary pace 410.

The system may utilize one or more cardiac response detection windows 455, 456, 460, 461 as illustrated in FIG. 3. A cardiac pacing response method that discriminates non-captured intrinsic beats in accordance with embodiments of the invention involves determining if one or more peak values of the cardiac response signal falls, or does not fall, within one or more cardiac response detection windows 455, 456, 460, 461. In this embodiment, the cardiac response detection windows 455, 456, 460, 461 are areas defined in terms of amplitude and time. In other embodiments, different or additional parameters may be used in addition to, or in place of the parameters of amplitude and time.

In the example of FIG. 3, the system may classify a cardiac response as capture if a peak value of the cardiac signal is detected in the first capture detection window 455 and a peak value of the cardiac signal is detected in the second capture detection window 456. If a cardiac signal peak is detected in the first non-captured intrinsic detection window 460, or the second non-captured intrinsic detection window 461, the cardiac response may be classified as noncapture with non-captured intrinsic activation. Otherwise, the beat may be classified as a fusion/pseudofusion beat, or further discriminated.

Devices and methods that discriminate non-captured intrinsic beats during evoked response detection and classification in accordance with embodiments of the present invention may involve the use of one or more noise detection windows 435, 436 for further discrimination of cardiac waveforms. If signal peaks fall within the cardiac response classification windows 455, 456, 460, 461, then the system checks for peaks opposite in polarity and comparable in magnitude to the cardiac response signal peaks.

FIG. 3 illustrates noise detection windows 435, 436. The noise detection windows 435, 436 may be any shape or size. For example, the noise detection windows 435, 436 may be the same size and/or shape as a corresponding capture detection window 455, 456 in a particular time interval 420, 450, or may be a different size and/or shape. Methods and systems involving noise detection windows, aspects of which may be utilized in connection with the embodiments of the present invention are described in commonly owned U.S. Pat. No. 7,765,004, which is incorporated herein by reference.

Figure 4:
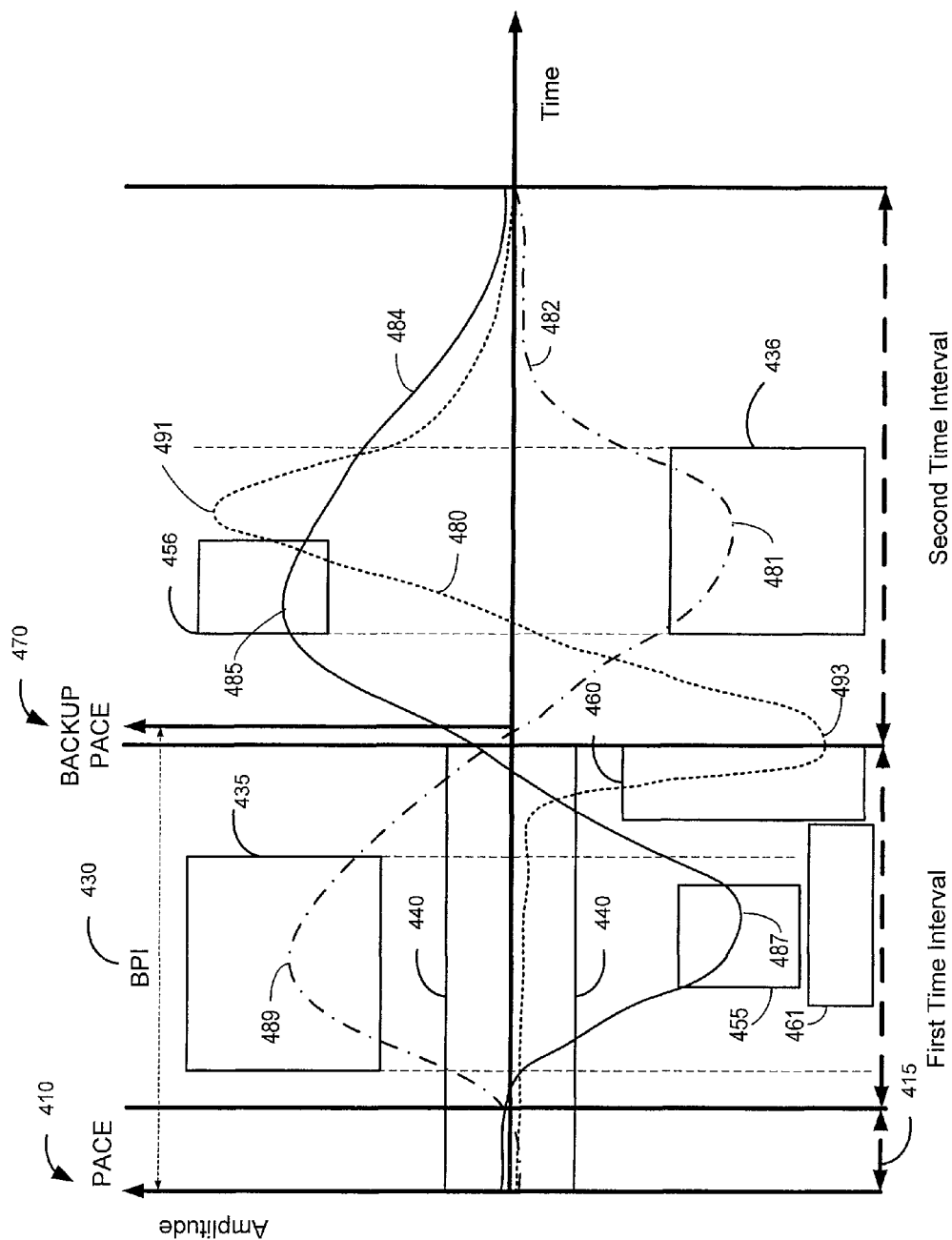
FIG. 4 illustrates cardiac response waveform portions superimposed over the graph in FIG. 3 in accordance with embodiments of the invention.

FIG. 4 illustrates three representative cardiac response waveform portions superimposed over the graph illustrated in FIG. 3. A non-captured intrinsic beat 480, a PVC beat 482, and a captured beat 484 are drawn, illustrating waveform parameters useful for discriminating non-captured intrinsic beats during cardiac pacing response classification in accordance with the present invention. The waveform parameters of the PVC beat 482 illustrated in the graph of FIG. 4 include, but are not limited to, a negative peak amplitude 481 within the second noise detection window 436 during the second time interval 450, and a positive peak 489 within the first noise detection window 435 during the first time interval 420.

The waveform parameters of the non-captured intrinsic beat 480 illustrated in the graph of FIG. 4 include, but are not limited to, a negative peak amplitude 493 within the first intrinsic detection window 460. The waveform parameters of the captured beat 484 illustrated in the graph of FIG. 4 include, but are not limited to, a negative peak amplitude 487 within the first capture detection window 455 during the first time interval 420, and a positive peak 485 within the second capture detection window 456 during the second time interval 450.

As is evident in FIG. 4, the non-captured intrinsic beat 480 and the captured beat 484 have morphologies similar enough that they may be confused if discrimination of non-captured intrinsic beats during evoked response detection and classification is not performed in accordance with embodiments of the present invention.

First and second intrinsic detection windows 460, 461 are provided in accordance with embodiments of the present invention to perform intrinsic discrimination. In some scenarios, the non-captured intrinsic beat 480 has a greater negative peak amplitude than the captured beat 484. The second intrinsic detection window 461 is defined in both time duration and amplitude breadth to discriminate arrival of a non-captured intrinsic beat 480, having a relatively larger negative peak, within the time frame of the capture detection window 455.

In some scenarios, as illustrated by the intrinsic waveform 480 of FIG. 4, the negative peak 493 of the intrinsic beat 480 occurs slightly later than the negative peak 487 of the captured beat signal 484. A first intrinsic detection window 460 that begins after the first capture detection window 455 discriminates intrinsic beats from capture beats. Providing one or more non-captured intrinsic beat capture detection windows in accordance with the present invention improves the discrimination capabilities of cardiac devices and reduces or eliminates the inclusion of undesired response signals during capture threshold testing, capture verification, template initialization and/or updating, and/or for other purposes when non-captured intrinsic beat discrimination is desirable.

The parameters of the intrinsic detection windows, including shape, area, and/or position may be selected based on the estimated or known morphology of cardiac signals associated with noncaptured intrinsic beats. Determination of the detection window parameters may be based on clinical data or on data acquired from the patient.

In one embodiment, the intrinsic detection window parameters are based on the relative timing of the capture detection window. Intrinsic activity generally occurs slightly later than the captured activity. Therefore, the intrinsic detection window may be arranged to occur just after the capture detection window, for example, in the first classification interval.

Patient conditions may affect the selected parameters of the intrinsic detection windows. For patients with intact AV conduction, for example, the intrinsic detection window parameters may be selected based on this information. In one implementation, for patients with known AV delay, the intrinsic detection window may be positioned to occur at a predetermined time following atrial activity.

The embodiments of the present system illustrated herein are generally described as being implemented in a patient implantable medical device such as a pacemaker/defibrillator that may operate in numerous pacing modes known in the art. Various types of single and multiple chamber implantable cardiac defibrillators are known in the art and may be used in connection with cardiac devices and methods that discriminate non-captured intrinsic beats during evoked response detection and classification in accordance with the present invention. The methods of the present invention may also be implemented in a variety of implantable or patient-external cardiac rhythm management devices, including single and multi chamber pacemakers, defibrillators, cardioverters, biventricular pacemakers, cardiac resynchronizers, and cardiac monitoring systems, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Figure 5:
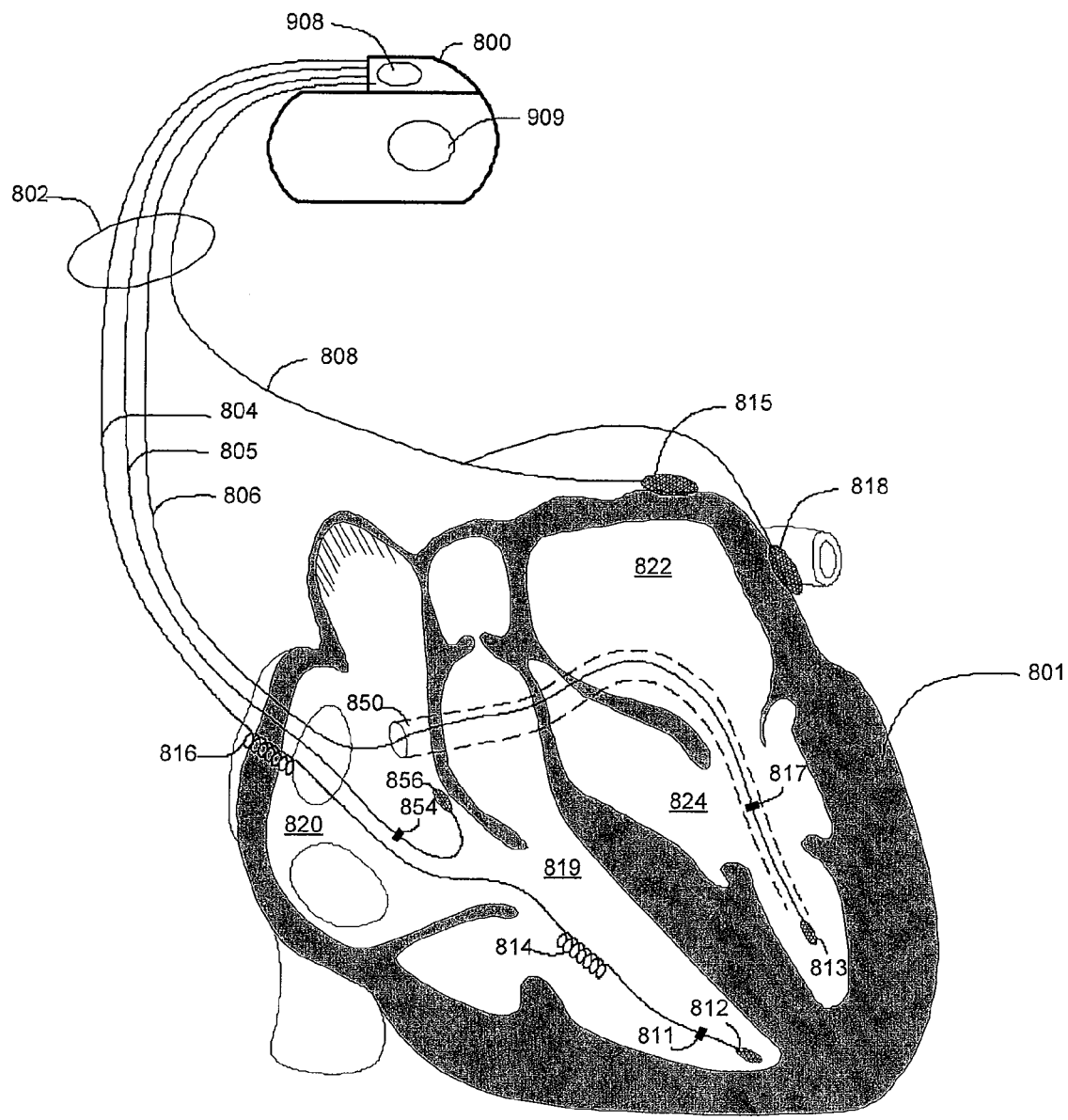
FIG. 5 is a partial view of one embodiment of an implantable medical device in accordance with embodiments of the invention.

Referring now to FIG. 5 of the drawings, there is shown a cardiac rhythm management system that may be used to implement methods that discriminate non-captured intrinsic beats during evoked response detection and cardiac pacing response classification in accordance with the present invention. The cardiac rhythm management system in FIG. 5 includes a pacemaker/defibrillator 800 electrically and physically coupled to a lead system 802. The housing and/or header of the pacemaker/defibrillator 800 may incorporate one or more electrodes 908, 909 used to provide electrical stimulation energy to the heart and to sense cardiac electrical activity. The pacemaker/defibrillator 800 may utilize all or a portion of the pacemaker/defibrillator housing as a can electrode 909. The pacemaker/defibrillator 800 may include an indifferent electrode 908 positioned, for example, on the header or the housing of the pacemaker/defibrillator 800. If the pacemaker/defibrillator 800 includes both a can electrode 909 and an indifferent electrode 908, the electrodes 908, 909 typically are electrically isolated from each other.

The lead system 802 is used to detect electric cardiac signals produced by the heart 801 and to provide electrical energy to the heart 801 under certain predetermined conditions to treat cardiac arrhythmias. The lead system 802 may include one or more electrodes used for pacing, sensing, and/or defibrillation. In the embodiment shown in FIG. 5, the lead system 802 includes an intracardiac right ventricular (RV) lead system 804, an intracardiac right atrial (RA) lead system 805, an intracardiac left ventricular (LV) lead system 806, and an extracardiac left atrial (LA) lead system 808. The lead system 802 of FIG. 5 illustrates one embodiment that may be used in connection with the feature determination methodologies described herein. Other leads and/or electrodes may additionally or alternatively be used.

The lead system 802 may include intracardiac leads 804, 805, 806 implanted in a human body with portions of the intracardiac leads 804, 805, 806 inserted into a heart 801. The intracardiac leads 804, 805, 806 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 5, the lead system 802 may include one or more extracardiac leads 808 having electrodes, e.g., epicardial electrodes, positioned at locations outside the heart for sensing and pacing one or more heart chambers.

The right ventricular lead system 804 illustrated in FIG. 5 includes an SVC-coil 816, an RV-coil 814, an RV-ring electrode 811, and an RV-tip electrode 812. The right ventricular lead system 804 extends through the right atrium 820 and into the right ventricle 819. In particular, the RV-tip electrode 812, RV-ring electrode 811, and RV-coil electrode 814 are positioned at appropriate locations within the right ventricle 819 for sensing and delivering electrical stimulation pulses to the heart 801. The SVC-coil 816 is positioned at an appropriate location within the right atrium chamber 820 of the heart 801 or a major vein leading to the right atrial chamber 820 of the heart 801.

In one configuration, the RV-tip electrode 812 referenced to the can electrode 909 may be used to implement unipolar pacing and/or sensing in the right ventricle 819. Bipolar pacing and/or sensing in the right ventricle may be implemented using the RV-tip 812 and RV-ring 811 electrodes. In yet another configuration, the RV-ring 811 electrode may optionally be omitted, and bipolar pacing and/or sensing may be accomplished using the RV-tip electrode 812 and the RV-coil 814, for example. The RV-coil 814 and the SVC-coil 816 are defibrillation electrodes.

The left ventricular lead 806 includes an LV distal electrode 813 and an LV proximal electrode 817 located at appropriate locations in or about the left ventricle 824 for pacing and/or sensing the left ventricle 824. The left ventricular lead 806 may be guided into the right atrium 820 of the heart via the superior vena cava. From the right atrium 820, the left ventricular lead 806 may be deployed into the coronary sinus ostium, the opening of the coronary sinus 850. The lead 806 may be guided through the coronary sinus 850 to a coronary vein of the left ventricle 824. This vein is used as an access pathway for leads to reach the surfaces of the left ventricle 824, which are not directly accessible from the right side of the heart. Lead placement for the left ventricular lead 806 may be achieved via subclavian vein access and a preformed guiding catheter for insertion of the LV electrodes 813, 817 adjacent to the left ventricle.

Unipolar pacing and/or sensing in the left ventricle may be implemented, for example, using the LV distal electrode referenced to the can electrode 909. The LV distal electrode 813 and the LV proximal electrode 817 may be used together as bipolar sense and/or pace electrodes for the left ventricle. The left ventricular lead 806 and the right ventricular lead 804, in conjunction with the pacemaker/defibrillator 800, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 805 includes an RA-tip electrode 856 and an RA-ring electrode 854 positioned at appropriate locations in the right atrium 820 for sensing and pacing the right atrium 820. In one configuration, the RA-tip 856 referenced to the can electrode 909, for example, may be used to provide unipolar pacing and/or sensing in the right atrium 820. In another configuration, the RA-tip electrode 856 and the RA-ring electrode 854 may be used to provide bipolar pacing and/or sensing.

FIG. 5 illustrates one embodiment of a left atrial lead system 808. In this example, the left atrial lead 808 is implemented as an extracardiac lead with LA distal 818 and LA proximal 815 electrodes positioned at appropriate locations outside the heart 801 for sensing and pacing the left atrium 822. Unipolar pacing and/or sensing of the left atrium may be accomplished, for example, using the LA distal electrode 818 to the can 909 pacing vector. The LA proximal 815 and LA distal 818 electrodes may be used together to implement bipolar pacing and/or sensing of the left atrium 822.

Figure 6:
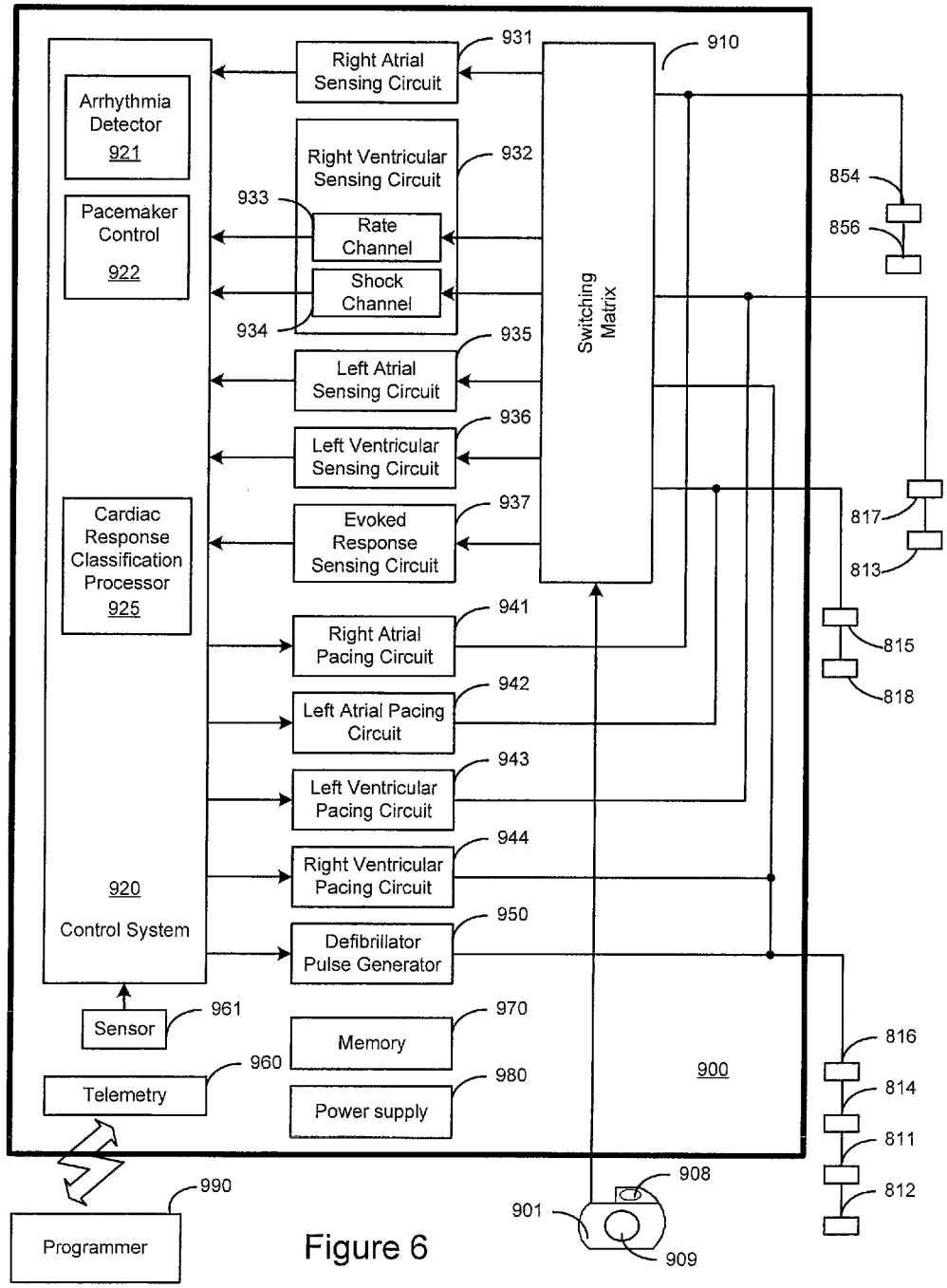
FIG. 6 is a block diagram of an implantable medical device that may be used for discrimination of non-captured intrinsic beats during evoked response detection and classification in accordance with embodiments of the invention.

Referring now to FIG. 6, there is shown an embodiment of a cardiac pacemaker/defibrillator 900 suitable for implementing non-captured intrinsic cardiac response detection and classification methods of the present invention. FIG. 6 shows a cardiac pacemaker/defibrillator 900 divided into functional blocks. It is understood by those skilled in the art that there exist many possible configurations in which these functional blocks can be arranged. The example depicted in FIG. 6 is one possible functional arrangement. Other arrangements are also possible. For example, more, fewer, or different functional blocks may be used to describe a cardiac pacemaker/defibrillator suitable for implementing the methodologies for feature determination in accordance with the present invention. In addition, although the cardiac pacemaker/defibrillator 900 depicted in FIG. 6 contemplates the use of a programmable microprocessor-based logic circuit, other circuit implementations may be utilized.

The cardiac pacemaker/defibrillator 900 depicted in FIG. 6 includes circuitry for receiving cardiac signals from a heart and delivering electrical stimulation energy to the heart in the form of pacing pulses or defibrillation shocks. In one embodiment, the circuitry of the cardiac pacemaker/defibrillator 900 is encased and hermetically sealed in a housing 901 suitable for implanting in a human body. Power to the cardiac pacemaker/defibrillator 900 is supplied by an electrochemical battery 980. A connector block (not shown) is attached to the housing 901 of the cardiac pacemaker/defibrillator 900 to allow for the physical and electrical attachment of the lead system conductors to the circuitry of the cardiac pacemaker/defibrillator 900.

The cardiac pacemaker/defibrillator 900 may be a programmable microprocessor-based system, including a control system 920 and a memory 970. The memory 970 may store parameters for various pacing, defibrillation, and sensing modes, along with other parameters. Further, the memory 970 may store data indicative of cardiac signals received by other components of the cardiac pacemaker/defibrillator 900. The memory 970 may be used, for example, for storing historical EGM and therapy data. The historical data storage may include, for example, data obtained from long-term patient monitoring used for trending and/or other diagnostic purposes. Historical data, as well as other information, may be transmitted to an external programmer unit 990 as needed or desired.

The control system 920 and memory 970 may cooperate with other components of the cardiac pacemaker/defibrillator 900 to control the operations of the cardiac pacemaker/defibrillator 900. The control system depicted in FIG. 6 incorporates a cardiac response classification processor 925 for classifying cardiac responses to pacing stimulation. The cardiac response classification processor performs the function of discriminating non-captured intrinsic responses for pacing response classification in accordance with embodiments of the invention. The control system 920 may include additional functional components including a pacemaker control circuit 922, an arrhythmia detector 921, along with other components for controlling the operations of the cardiac pacemaker/defibrillator 900.

Telemetry circuitry 960 may be implemented to provide communications between the cardiac pacemaker/defibrillator 900 and an external programmer unit 990. In one embodiment, the telemetry circuitry 960 and the programmer unit 990 communicate using a wire loop antenna and a radio frequency telemetric link, as is known in the art, to receive and transmit signals and data between the programmer unit 990 and the telemetry circuitry 960. In this manner, programming commands and other information may be transferred to the control system 920 of the cardiac pacemaker/defibrillator 900 from the programmer unit 990 during and after implant. In addition, stored cardiac data pertaining to capture threshold, capture detection, and/or cardiac response classification, for example, along with other data, may be transferred to the programmer unit 990 from the cardiac pacemaker/defibrillator 900.

The telemetry circuitry 960 may provide for communication between the cardiac pacemaker/defibrillator 900 and an advanced patient management (APM) system. The advanced patient management system allows physicians or other personnel to remotely and automatically monitor cardiac and/or other patient conditions. In one example, a cardiac pacemaker/defibrillator, or other device, may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

In the embodiment of the cardiac pacemaker/defibrillator 900 illustrated in FIG. 6, electrodes RA-tip 856, RA-ring 854, RV-tip 812, RV-ring 811, RV-coil 814, SVC-coil 816, LV distal electrode 813, LV proximal electrode 817, LA distal electrode 818, LA proximal electrode 815, indifferent electrode 908, and can electrode 909 are coupled through a switch matrix 910 to sensing circuits 931-937.

A right atrial sensing circuit 931 serves to detect and amplify electrical signals from the right atrium of the heart. Bipolar sensing in the right atrium may be implemented, for example, by sensing voltages developed between the RA-tip 856 and the RA-ring 854. Unipolar sensing may be implemented, for example, by sensing voltages developed between the RA-tip 856 and the can electrode 909. Outputs from the right atrial sensing circuit are coupled to the control system 920.

A right ventricular sensing circuit 932 serves to detect and amplify electrical signals from the right ventricle of the heart. The right ventricular sensing circuit 932 may include, for example, a right ventricular rate channel 933 and a right ventricular shock channel 934. Right ventricular cardiac signals sensed through use of the RV-tip 812 electrode are right ventricular near-field signals and are denoted RV rate channel signals. A bipolar RV rate channel signal may be sensed as a voltage developed between the RV-tip 812 and the RV-ring 811. Alternatively, bipolar sensing in the right ventricle may be implemented using the RV-tip electrode 812 and the RV-coil 814. Unipolar rate channel sensing in the right ventricle may be implemented, for example, by sensing voltages developed between the RV-tip 812 and the can electrode 909.

Right ventricular cardiac signals sensed through use of the defibrillation electrodes are far-field signals, also referred to as RV morphology or RV shock channel signals. More particularly, a right ventricular shock channel signal may be detected as a voltage developed between the RV-coil 814 and the SVC-coil 816. A right ventricular shock channel signal may also be detected as a voltage developed between the RV-coil 814 and the can electrode 909. In another configuration, the can electrode 909 and the SVC-coil electrode 816 may be electrically shorted and a RV shock channel signal may be detected as the voltage developed between the RV-coil 814 and the can electrode 909/SVC-coil 816 combination. Outputs from the right ventricular sensing circuit 932 are coupled to the control system 920. In one embodiment of the invention, rate channel signals and shock channel signals may be used to develop morphology templates for analyzing cardiac signals. In this embodiment, rate channel signals and shock channel signals may be transferred from the right ventricular sensing circuit 932 to the control system 920 and analyzed for arrhythmia detection.

Left atrial cardiac signals may be sensed through the use of one or more left atrial electrodes 815, 818, which may be configured as epicardial electrodes. A left atrial sensing circuit 935 serves to detect and amplify electrical signals from the left atrium of the heart. Bipolar sensing and/or pacing in the left atrium may be implemented, for example, using the LA distal electrode 818 and the LA proximal electrode 815. Unipolar sensing and/or pacing of the left atrium may be accomplished, for example, using the LA distal electrode 818 to the can vector 909 or the LA proximal electrode 815 to the can vector 909.

A left ventricular sensing circuit 936 serves to detect and amplify electrical signals from the left ventricle of the heart. Bipolar sensing in the left ventricle may be implemented, for example, by sensing voltages developed between the LV distal electrode 813 and the LV proximal electrode 817. Unipolar sensing may be implemented, for example, by sensing voltages developed between the LV distal electrode 813 or the LV proximal electrode 817 and the can electrode 909.

Optionally, an LV coil electrode (not shown) may be inserted into the patient's cardiac vasculature, e.g., the coronary sinus, adjacent to the left heart. Signals detected using combinations of the LV electrodes 813, 817, LV coil electrode (not shown), and/or the can electrode 909 may be sensed and amplified by the left ventricular sensing circuitry 936. The output of the left ventricular sensing circuit 936 is coupled to the control system 920.

The outputs of the switching matrix 910 may be operated to couple selected combinations of electrodes 811, 812, 813, 814, 815, 816, 817, 818, 856, 854 to an evoked response sensing circuit 937. The evoked response sensing circuit 937 serves to sense and amplify voltages developed using various combinations of electrodes for discrimination of various cardiac responses to pacing in accordance with embodiments of the invention. The cardiac response classification processor 925 may analyze the output of the evoked response sensing circuit 937 to implement feature association and cardiac pacing response classification in accordance with embodiments of the invention.

Various combinations of pacing and sensing electrodes may be utilized in connection with pacing and sensing the cardiac signal following the pace pulse to classify the cardiac response to the pacing pulse. For example, in some embodiments, a first electrode combination is used for pacing a heart chamber and a second electrode combination is used to sense the cardiac signal following pacing. In other embodiments, the same electrode combination is used for pacing and sensing. Use of different electrodes for pacing and sensing in connection with capture verification is described in commonly owned U.S. Pat. No. 6,128,535, which is incorporated herein by reference.

The pacemaker control circuit 922, in combination with pacing circuitry for the left atrium, right atrium, left ventricle, and right ventricle 941, 942, 943, 944, may be implemented to selectively generate and deliver pacing pulses to the heart using various electrode combinations. The pacing electrode combinations may be used to effect bipolar or unipolar pacing pulses to a heart chamber using one of the pacing vectors as described above. In some implementations, the cardiac pacemaker/defibrillator 900 may include a sensor 961 that is used to sense the patient's hemodynamic need. The pacing output of the cardiac pacemaker/defibrillator may be adjusted based on the sensor 961 output.

The electrical signal following the delivery of the pacing pulses may be sensed through various sensing vectors coupled through the switch matrix 910 to the evoked response sensing circuit 937 and used to classify the cardiac response to pacing. The cardiac response may be classified as one of a captured response, a non-captured response, a non-captured response with intrinsic activation, and a fusion/pseudofusion beat, for example.

Subcutaneous electrodes may provide additional sensing vectors useable for cardiac response classification. In one implementation, a cardiac rhythm management system may involve a hybrid system including an intracardiac device configured to pace the heart and an extracardiac device, e.g., a subcutaneous defibrillator, configured to perform functions other than pacing. The extracardiac device may be employed to detect and classify the cardiac response to pacing based on signals sensed using subcutaneous electrode arrays. The extracardiac and intracardiac devices may operate cooperatively with communication between the devices occurring over a wireless link, for example. Examples of subcutaneous electrode systems and devices are described in commonly owned U.S. Patent Publication Nos. 2004/0230229 and 2004/0230230, which are hereby incorporated herein by reference in their respective entireties.

Figure 7:
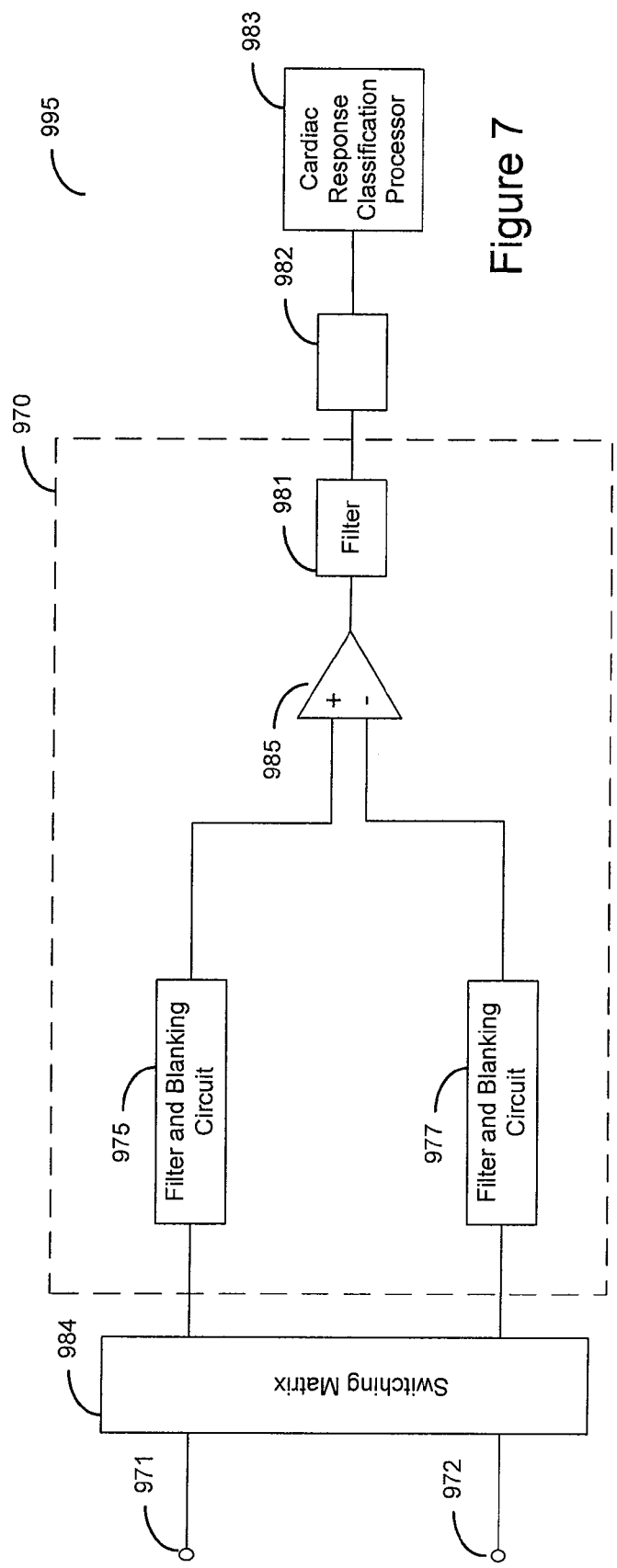
FIG. 7 is a schematic diagram of a circuit that may be used to sense a cardiac signal following the delivery of a pacing stimulation and to classify the cardiac response to the pacing stimulation according to embodiments of the invention.

FIG. 7 illustrates a block diagram of the circuit 995 that may be used to sense cardiac signals following the delivery of a pacing stimulation and classify the cardiac response to the pacing stimulation according to embodiments of the invention. A switch matrix 984 is used to couple the cardiac electrodes 971, 972 in various combinations discussed above to the sensing portion 970 of the cardiac response classification circuit 995. The sensing portion 970 includes filtering and blanking circuitry 975, 977, sense amplifier 985, band pass filter 981, and window generation and signal characteristic detector 982. The window generation and signal characteristic detector 982 is coupled to a cardiac response classification processor 983.

A control system, e.g., the control system 920 depicted in FIG. 6, is operatively coupled to components of the cardiac sensing circuit 995 and controls the operation of the circuit 995, including the filtering and blanking circuits 975, 977. Following delivery of the pacing stimulation, the blanking circuitry 975, 977 operates for a sufficient duration and then allows detection of a cardiac signal responsive to the pacing stimulation. The cardiac signal is filtered, amplified, and converted from analog to digital form. The digitized signal is communicated to the cardiac response classification processor 983, which operates in cooperation with other components of the control system 920 (FIG. 6) to classify cardiac responses to pacing according to embodiments of the invention.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of operating a cardiac device to classify a cardiac response to a pacing pulse, comprising:
   delivering the pacing pulse to a heart;
   sensing a cardiac signal following delivery of the pacing pulse, the cardiac signal having an amplitude that varies over time;
   determining if a peak of the amplitude of the sensed cardiac signal falls within one of a plurality of detection windows associated with a non-captured intrinsic response, each of the intrinsic detection windows finitely bounded in time and amplitude;

classifying the cardiac response to the pacing pulse as the non-captured intrinsic response if the sensed cardiac signal peak amplitude falls within one of the intrinsic detection windows; and delivering pacing therapy based on the cardiac response classification.

2. The method of claim 1, wherein at least one of the intrinsic detection windows is coextensive in amplitude and non-overlapping with respect to a capture detection window, the capture detection window finitely bounded in time and amplitude.

3. The method of claim 1, wherein at least one of the intrinsic detection windows is coextensive in time and non-overlapping with respect to a capture detection window, the capture detection window finitely bounded in time and amplitude.

4. The method of claim 1, wherein:
at least one of the intrinsic detection windows is coextensive in amplitude and non-overlapping with respect to a capture detection window, the capture detection window finitely bounded in time and amplitude; and
at least one of the intrinsic detection windows is coextensive in time and non-overlapping with respect to a capture detection window, the capture detection window finitely bounded in time and amplitude.

5. The method of claim 1, wherein the sensed cardiac signal is filtered, amplified and/or digitized from a raw cardiac signal that is detected via one or more electrodes positioned in a human body.

6. The method of claim 1, further comprising:
determining if the peak of the sensed cardiac signal falls within a first capture detection window;
determining if a peak of opposite polarity falls within a second capture detection window, each of the first and second capture detection windows finitely bounded by time and amplitude and associated with a captured response; and
classifying the cardiac response to the pacing pulse as the captured response if the peaks of the sensed cardiac signal respectively fall within the first and second capture detection windows.

7. The method of claim 1, further comprising discriminating the non-captured intrinsic response from unknown cardiac activity.

8. The method of claim 1, further comprising discriminating the cardiac response as a fusion beat if the cardiac response is not a captured beat or a non-captured intrinsic beat.

9. The method of claim 1, further comprising discriminating the non-captured intrinsic response from a premature ventricular activation.

10. The method of claim 1, further comprising:
determining if the peak falls in at least one noise detection window; and
classifying the cardiac response as unknown sensed cardiac signal behavior if the sensed cardiac signal peak is detected in the at least one noise detection window.

11. The method of claim 1, wherein parameters of at least one intrinsic detection window are selected based on patient conditions.

12. A method of operating a cardiac device to classify a cardiac response to a pacing pulse, comprising:
delivering the pacing pulse to a heart;
sensing a cardiac signal following delivery of the pacing pulse;
determining if a peak of the sensed cardiac signal falls within a first capture detection window;
determining if a peak of opposite polarity falls within a second capture detection window, each of the first and second capture detection windows finitely bounded by time and amplitude and associated with a captured response; and
classifying the cardiac response to the pacing pulse as the captured response if the peaks of the sensed cardiac signal respectively fall within the first and second capture detection windows.

13. A system for delivering a pacing therapy to a heart, comprising:
a sensing block for sensing a cardiac signal from the heart following delivery of a pacing pulse to the heart, the cardiac signal having an amplitude that varies over time;
a processor coupled to the sensing block, the processor configured to determine if a peak of the amplitude of the sensed cardiac signal falls within one of a plurality of detection windows associated with a non-captured intrinsic response, each of the intrinsic detection windows finitely bounded in time and amplitude;
the processor further configured to classify the cardiac response to the pacing pulse as the non-captured intrinsic response if the sensed cardiac signal peak amplitude falls within one of the intrinsic detection windows; and
a therapy block configured to deliver a pacing therapy based on the cardiac response classification.

14. The system of claim 13, wherein at least one of the intrinsic detection windows is coextensive in amplitude and non-overlapping with respect to a capture detection window, the capture detection window finitely bounded in time and amplitude.

15. The system of claim 13, wherein at least one of the intrinsic detection windows is coextensive in time and non-overlapping with respect to a capture detection window, the capture detection window finitely bounded in time and amplitude.

16. The system of claim 13, wherein:
at least one of the intrinsic detection windows is coextensive in amplitude and non-overlapping with respect to a capture detection window, the capture detection window finitely bounded in time and amplitude; and
at least one of the intrinsic detection windows is coextensive in time and non-overlapping with respect to a capture detection window, the capture detection window finitely bounded in time and amplitude.

17. The system of claim 13, wherein the processor is further configured to determine if the peak of the sensed cardiac signal falls within a first capture detection window and to determine if a peak of opposite polarity falls within a second capture detection window, each of the first and second capture detection windows finitely bounded by time and amplitude and associated with a captured response and to classify the cardiac response to the pacing pulse as the captured response if the peaks of the sensed cardiac signal respectively fall within the first and second capture detection windows.

18. The system of claim 13, wherein the processor is further configured to determine if the sensed cardiac signal peak falls in at least one noise detection window and to classify the cardiac response as unknown sensed cardiac signal behavior if the sensed cardiac signal peak is detected in the at least one noise detection window.

19. The system of claim 13, wherein the processor is further configured to discriminate the cardiac response as a fusion beat if the cardiac response is not a captured beat or a non-captured intrinsic beat.

20. The system of claim 13, wherein the processor is further configured to discriminate the non-captured intrinsic response from a premature ventricular activation.

\* \* \* \* \*